United States Patent [19]
Held

[11] Patent Number: 4,763,940
[45] Date of Patent: Aug. 16, 1988

[54] DOCUMENT HANDLING AID

[76] Inventor: Curtis N. Held, Rte. 1, Box 350, St. Joseph, Wis. 54082

[21] Appl. No.: 77,029

[22] Filed: Jul. 20, 1987

Related U.S. Application Data

[63] Continuation of Ser. No. 840,331, Mar. 17, 1986, abandoned.

[51] Int. Cl.⁴ .................... A41D 13/08; A61F 13/10
[52] U.S. Cl. ........................................ 294/25; 2/21
[58] Field of Search .............. 294/1.1, 25; 2/21, 163; 15/227; 30/298; 131/258; 223/101; 273/54 B; 401/8

[56] References Cited

U.S. PATENT DOCUMENTS

| | | | |
|---|---|---|---|
| 135,305 | 1/1873 | Ackley et al. | 294/25 X |
| 207,708 | 9/1878 | Boyer | 294/25 |
| 495,790 | 4/1893 | Durham | 223/101 |
| 560,377 | 5/1896 | Stewart | 2/21 X |
| 835,803 | 11/1906 | Witten | 2/21 X |
| 1,000,226 | 8/1911 | Arwine | 294/25 X |
| 1,109,796 | 9/1914 | Sills | 2/21 X |
| 1,399,870 | 12/1921 | Pearce | 294/25 |
| 1,417,414 | 5/1922 | Sanders | 2/21 |
| 1,484,489 | 2/1924 | Givens | 294/25 |
| 1,854,047 | 4/1932 | Kurtz, Jr. | 2/21 X |
| 1,980,635 | 11/1934 | Rasmussen et al. | 2/21 |
| 2,358,440 | 9/1944 | Bowman | 2/21 |
| 2,363,216 | 11/1944 | Wong | 294/25 |
| 2,462,208 | 2/1949 | Meyer | 294/25 |
| 2,502,266 | 3/1950 | Mateo | 2/21 |
| 2,564,349 | 8/1951 | Thal | 223/101 X |
| 2,740,121 | 4/1956 | Seidel | 2/21 |
| 3,343,177 | 9/1967 | Bellamy | 2/21 |

FOREIGN PATENT DOCUMENTS 15435 of 1892 United Kingdom ............... 223/101

OTHER PUBLICATIONS

Frederick-Sherry Office Products, 1985 Catalog, cover and p. 32.
Bertelson Bros. Inc., 1985 Catalog, cover and p. 530.
Miller-Davis Co., 1983 Catalog, cover and p. 61B.
Commercial Office Products, Inc., 1984 Catalog, cover and p. 115.

Primary Examiner—Johnny D. Cherry
Attorney, Agent, or Firm—Kinney & Lange

[57] ABSTRACT

A document handling aid has a resilient tubular body with first and second joined body sections. Both ends of the tubular body are open so that when mounted on a finger, the tip of the finger protrudes from the first body section adjacent thereto. The second body section grips the finger about the first knuckle and has a plurality of generally parallel longitudinal cuts therethrough to permit enhanced radial expansion of the tubular body adjacent the first knuckle of the finger.

2 Claims, 1 Drawing Sheet

DOCUMENT HANDLING AID

This is a continuation of application Ser. No. 840,331, filed Mar. 17, 1986 (now abandoned).

REFERENCE TO CO-PENDING APPLICATION

Reference is hereby made to copending patent application Ser. No. 06/742,403, entitled "Document Handling Aid," filed June 7, 1985 by Applicant, now abandoned.

BACKGROUND OF THE INVENTION

1. Field of the Invention

The present invention relates to finger tip mounted document handling aids.

2. Description of the Prior Art

In many vocations, continuous handling of documents and other materials by hand is required. To enhance the gripping ability of fingers, finger cots or rubber fingertips have been used. Such devices typically consist of a conical device which slips over the end of a finger and has a closed outer end. This design has proved unacceptable in some applications because its closed outer end prevents an operator from "feeling" with the finger. In addition, this design is easily caught on document pages or "pigeonhole" edges and dislodged from the finger. The operator then loses time in replacing the finger cot which thereby reduces the operator's efficiency in performing his or her primary work tasks.

Improvements upon this basic design have been attempted. The patents listed below show various finger cot designs which have been developed for different tasks:

| U.S. Pat. No. | Inventor | Issued |
| --- | --- | --- |
| 207,708 | J. S. Boyer | 9/3/1878 |
| 835,803 | A. P. Witten | 11/13/06 |
| 1,109,796 | J. F. Sills | 9/8/14 |
| 1,399,870 | A. Pearce | 12/13/21 |
| 1,484,489 | M. A. Givens | 2/19/24 |
| 1,980,635 | W. R. Rasmussen et al. | 11/13/34 |
| 2,358,440 | E. F. Bowman | 9/19/44 |
| 2,363,216 | G. B. Wong | 11/21/44 |
| 2,502,266 | L. Mateo | 3/28/50 |
| 3,343,177 | A. C. Bellamy | 9/26/67 |

While some of the devices shown in these patents attempt to provide a finger cot which firmly engages the finger to prevent dislodgment, these designs have proved unsuitable.

Many finger cots or fingertips are composed of rubberized material which stretches to allow finger bending and also gripping of the finger by the device, but that alone has proved insufficient. U.S. Pat. No. 135,305, granted to Ackley, et al., on Jan. 28, 1873, shows a thumb-mounted "tobacco-topper" which has a single opening therein for accommodating the upper side of the knuckle of the wearer's thumb. When handling documents at high speeds in present day applications, however, such an opening to permit movement is simply not enough.

SUMMARY OF THE INVENTION

The present invention provides a finger mounted document handling aid which overcomes the disadvantages of the prior art. The document handling aid of the present invention comprises a longitudinally extending generally tubular and flexible body having first and second body sections. The flexible body is adopted to be longitudinally mounted upon a finger so that the first body section extends from a tip of the finger toward a first knuckle thereof, while the second body section envelopes the first knuckle. The tip of the finger protrudes out of the flexible body adjacent the first body section thereof and the second body section has a plurality of generally parallel longitudinal cuts therethrough to permit enhanced radial expansion of the second body section adjacent the first knuckle.

DETAILED DESCRIPTION OF THE PREFERRED EMBODIMENTS

Figure 1:
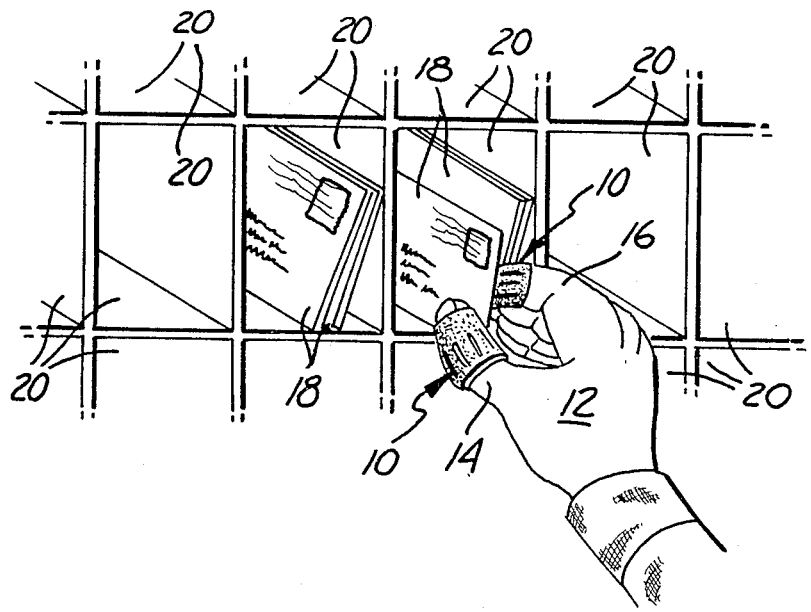
FIG. 1 is a pictorial view of the document handling aid of the present invention in use in sorting documents.

FIG. 1 illustrates a document handling aid 10 of the present invention in use. The document handling aid 10 can be used to aid any finger of an operator's hand 12 in sorting or handling documents or other materials, including a thumb 14 or forefinger 16. As seen, the document handling aid 10 fits over a finger adjacent its tip and covers most areas of the finger which would normally come into contact with documents or other items being handled by the wearer. As seen in FIG. 1, an operator is placing letters 18 into various cubbyholes or pigeonholes 20.

Figure 2:
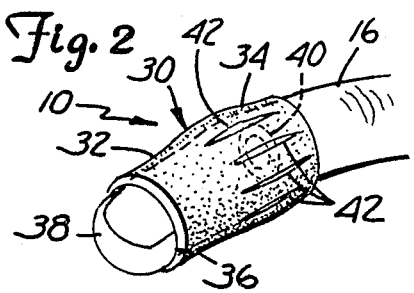
FIG. 2 is a pictorial view of the document handling aid of the present invention, mounted on a finger.
Figure 3:
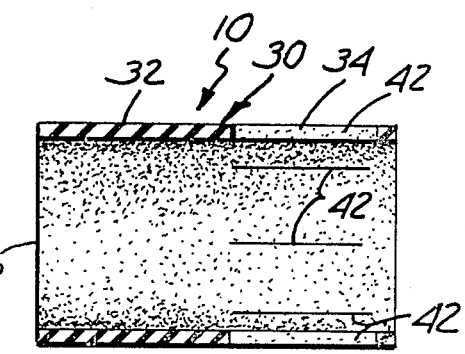
FIG. 3 is a longitudinal sectional view of the document handling aid, in an unstressed condition.

The document handling aid 10 consists of a longitudinally extending generally tubular and flexible body 30. The body is generally circular in lateral cross-section and although unitary, is divided into two main sections—a first section 32 and a second section 34 (as perhaps best seen in FIGS. 2 and 3). As seen in FIGS. 1 and 2, the first section 32 has an open end 36 through which a fingertip 38 (of finger 16) protrudes. The first section 32 of the tubular body 30 thus provides enhanced friction for document handling, while permitting the fingertip 38 to be used for tactile sensing.

As seen in FIG. 2, the finger 16 is longitudinally received within the tubular body 30. The second section 34 of the tubular body 30 is positioned to envelope or surround a first knuckle 40 of the finger 16, as illustrated in phantom in FIG. 2. When the document handling aid 10 is properly mounted on a finger 16 as seen in FIGS. 1 and 2, the first section 32 is proximate the tip 38 of the finger 16 and the second section 34 is adapted to grip the knuckle 40 and portions of the finger 16 immediately adjacent thereto.

The second section 34 of the tubular body 30 has a plurality of generally parallel longitudinal cuts or slots 42 extending completely therethrough. Although the second section 34 is comprised of a flexible material, these cuts permit additional expansion radially of the tubular body when the second section 34 thereof is secured about the first knuckle 40. This permits the wearer of the document handling aid 10 to more easily flex the finger 16 at its first knuckle 40 and also makes the document handling aid 10 more comfortable for its wearer, at no cost to the effectiveness in use of the document handling aid 10.

The document handling aid of the present invention shown in the accompanying drawings is generally tubular. Different shapes thereof are contemplated. In addition, nubs or ridges on the outside surfaces of the tubular body 30 enhance its frictional capabilities. The document handling aid 10 is also available in various sizes (lengths, and widths) to accommodate different sized fingers and wearers.

Although the present invention has been described with reference to preferred embodiments, workers skilled in the art will recognize that changes may be made in form and detail without departing from the spirit and scope of the invention.

What is claimed is:

1. A finger mounted document handling aid comprising a longitudinally extending, generally tubular and flexible body having first and second body sections, the flexible body being adapted to be longitudinally mounted upon a finger so that the first body section extends from a tip of the finger toward a first knuckle thereof and a second body section of size to envelope only said first knuckle, with a sufficient portion of the tip of the finger protruding out of a first end of the flexible body adjacent the first body section thereof to permit tactile sensing by the tip of the finger, the second body section extending from the first body section to a second end of the flexible body and having a plurality of fully internal, generally parallel longitudinal cuts therethrough to permit enhanced radial expansion and greater flexibility of the second body section adjacent the first knuckle, the end of each cut closest to the second end of the flexible body being spaced longitudinally from said second end.

2. In a finger-mounted document handling aid of the type having a generally tubular and flexible body adapted for longitudinal reception of a finger, the improvement comprising:

a first section of the flexible body which extends from proximate a tip of the finger toward a first knuckle thereof, with a sufficient portion of the tip of the finger protruding out of the flexible body adjacent the first section thereof to permit tactile sensing by the tip of the finger; and a second section of the flexible body of size to envelope only the first knuckle, with the second section having a plurality of generally parallel longitudinal spaced cuts therethrough to permit enhanced radial expansion and greater flexibility of the second section adjacent the first knuckle, each cut terminating internally within the second section of the flexible body.

* * * * *